United States Patent
Oddie

(10) Patent No.: US 8,557,588 B2
(45) Date of Patent: Oct. 15, 2013

(54) METHODS AND APPARATUS FOR SAMPLING AND DILUTING CONCENTRATED EMULSIONS

(75) Inventor: Gary Martin Oddie, St. Neots (GB)

(73) Assignees: Schlumberger Technology Corporation, Sugar Land, TX (US); Total S.A., Courbevoie (FR)

( * ) Notice: Subject to any disclaimer, the term of this patent is extended or adjusted under 35 U.S.C. 154(b) by 1306 days.

(21) Appl. No.: 11/691,690

(22) Filed: Mar. 27, 2007

(65) Prior Publication Data
US 2008/0236258 A1 Oct. 2, 2008

(51) Int. Cl.
*G01N 33/18* (2006.01)

(52) U.S. Cl.
USPC ............ 436/40; 436/39; 422/73; 73/54.01; 73/53.01; 73/64.56

(58) Field of Classification Search
USPC ......... 73/53.01, 64.56, 54.01; 436/39–40, 71; 422/73
See application file for complete search history.

(56) References Cited

U.S. PATENT DOCUMENTS

| | | | |
|---|---|---|---|
| 4,015,628 A | 4/1977 | Randolph | |
| 4,619,136 A | 10/1986 | Ortiz | |
| 5,007,297 A | 4/1991 | Sommer | |
| 5,140,527 A | 8/1992 | Jones et al. | |
| 5,265,643 A * | 11/1993 | Golestan et al. | 137/504 |
| 5,283,001 A * | 2/1994 | Gregoli et al. | 516/67 |
| 5,569,844 A | 10/1996 | Sowerby | |
| 5,831,150 A | 11/1998 | Sowerby et al. | |
| 5,907,108 A | 5/1999 | Garcia et al. | |
| 6,177,994 B1 | 1/2001 | Watson et al. | |
| 6,211,956 B1 * | 4/2001 | Nicoli | 356/337 |
| 6,286,376 B1 | 9/2001 | Davidson et al. | |
| 6,778,271 B2 | 8/2004 | Watson et al. | |
| 6,800,251 B2 | 10/2004 | Catterall et al. | |
| 6,916,658 B2 | 7/2005 | Li et al. | |
| 7,141,213 B1 | 11/2006 | Pang et al. | |
| 7,148,185 B2 | 12/2006 | Fu et al. | |
| 7,162,057 B1 | 1/2007 | Roth et al. | |
| 2004/0200986 A1 * | 10/2004 | Noritake et al. | 251/122 |
| 2004/0265177 A1 * | 12/2004 | Nicoli et al. | 422/73 |

FOREIGN PATENT DOCUMENTS

| | | |
|---|---|---|
| EP | 0214843 | 3/1987 |
| GB | 2359631 A | 8/2001 |
| WO | 0022407 | 4/2000 |
| WO | 0163094 A1 | 8/2001 |
| WO | 2007074225 | 7/2007 |
| WO | 2008021531 | 2/2008 |

* cited by examiner

*Primary Examiner* — Michael Marcheschi
*Assistant Examiner* — Jonathan Hurst

(57) ABSTRACT

Methods and apparatus are described for sampling and diluting concentrated emulsions, which may be oil-in-water emulsions, water-in-oil emulsions, or other concentrated emulsions. One method embodiment of the invention comprises obtaining a sample of a concentrated emulsion comprising a dispersed phase and a continuous phase fluid; measuring droplet concentration of the dispersed phase in the sample; and for droplet concentration of the sample greater than about 1000 ppm, diluting the sample with substantially pure continuous phase fluid, forming a first diluted emulsion. Methods of the invention include those wherein the obtaining of a sample comprises opening a fluid connection to a flowing stream comprising the concentrated emulsion, wherein the obtaining and diluting steps occur in real time.

14 Claims, 2 Drawing Sheets

METHODS AND APPARATUS FOR SAMPLING AND DILUTING CONCENTRATED EMULSIONS

BACKGROUND OF THE INVENTION

1. Field of Invention

The present invention relates to the field of droplet size distribution in concentrated emulsions, in particular flowing emulsions.

2. Related Art

Measurements of droplet size distribution in concentrated flowing emulsions, such as oil-in-water and water-in-oil emulsions and suspensions, are not possible without dilution to a level where the physics of the analysis method can interact with individual droplets without being dominated by second order effects such as multiple scattering. For concentrations of the dispersed phase (droplets) of less than 1000 ppm, several devices exist that use different physical methods for determining the droplet size distribution. Examples of these include direct imaging by light transmission; multi-angle two color light scattering; use of an electrical sensing zone; and ultrasonic scattering. In all of these known devices and methods, the inability to analyze more concentrated emulsions is caused by the complex interpretation required when the particles are very close together, when secondary effects such as multiple scattering and/or shadowing start to occur.

It would be an advance in the art if methods and apparatus could be developed that can sample a concentrated emulsion and dilute the concentrated emulsion without significantly affecting the droplet size distribution present in the concentrated emulsion.

SUMMARY OF THE INVENTION

In accordance with the present invention, methods and apparatus for sampling and diluting concentrated emulsions are presented that allow existing droplet size distribution measuring techniques to be employed. The emulsion may comprise any oil-in-water or water-in-oil emulsion, including, but not limited to emulsions comprising hydrocarbons (including sour hydrocarbons which may include hydrogen sulfide, mercaptans, and other sulfur-containing compounds), water, organic and/or inorganic solids, and may include micelles, macromolecules, globules, resins, asphaltenes, hydrocarbon and aqueous based fluids, drilling muds, frac fluids, and the like having multiple phases (solids and liquid). The emulsion may comprise one or more of each phase.

As used herein, the term "emulsion" means a dispersion of one liquid in a second immiscible liquid. The emulsion may be unstable or stable, or have any degree of stability, although apparatus and methods of the invention are particularly useful in sampling and diluting unstable emulsions (sometimes referred to herein as unstabilized emulsions). As used herein "concentrated", when referring to an emulsion, means the emulsion comprises droplets of dispersed phase at 1000 ppm or greater. A concentration less than 1000 ppm is considered a diluted emulsion. Since the majority of emulsions contain water as one of the phases, it is customary to classify emulsions into two types: the oil-in-water (O/W) type comprising droplets of oil dispersed in water, and the water-in-oil (W/O) type in which the phases are reversed. The continuous liquid is referred to herein as the continuous phase, and the liquid which is in the form of droplets is referred to herein as the dispersed phase. The invention is not limited to sampling and diluting of O/W and W/O emulsions, and either O/W or W/O emulsions may comprise other components, as discussed herein, such as surfactants, viscosity modifiers, and the like. A stable emulsion consisting of two pure liquids cannot be prepared; to achieve stability, a third component, an emulsifying agent, must be present. Generally, the introduction of an emulsifying agent will lower the interfacial tension of the two phases. A large number of emulsifying agents are known; they can be classified broadly into several groups. The largest group is that of the soaps, detergents, and other compounds whose basic structure is a paraffin chain terminating in a polar group. Some solid powders can act as emulsifiers by being wetted more by one phase than by the other. Whichever phase shows the greater wetting power will become the dispersion medium.

One aspect of the invention comprises methods of sampling and diluting a concentrated emulsion to form a dilute emulsion, one method comprising:
  (a) obtaining a sample of a concentrated emulsion comprising a dispersed phase and a continuous phase fluid;
  (b) measuring droplet concentration of the dispersed phase in the sample;
  (c) if the droplet concentration of the sample is less than about 1000 ppm, measuring droplet size distribution of the sample, and if the droplet concentration is greater than about 1000 ppm, diluting the sample with substantially pure continuous phase fluid, forming a first diluted emulsion; and
  (d) optionally measuring droplet size distribution of the first diluted emulsion.

Methods within the invention include those wherein if the droplet concentration of the first diluted emulsion is still greater than 1000 ppm, or if for some other reason a droplet size distribution is too difficult to accomplish using the chosen method of measuring droplet size distribution, then one or more further dilutions with continuous phase fluid may be performed, and the droplet size distribution re-measured. Methods within the invention include those wherein flows of the sample of concentrated emulsion, first diluted emulsion, and added continuous phase fluid are controlled using flow rate controlling valves designed to produce substantially constant flow rates irrespective of pressure drop through sampling lines, and the diluting flow rate may be independent of any of the pressures in the supply or sampling lines. An important feature is that all of the flow rate controlling valves (or other flow rate controlling means as described herein) are downstream of the dilution, sampling and measurement process. Thus the fluid being tested does not feel any shear from any flow controlling device prior or during measurement of droplet size distribution. In certain embodiments, the concentrated emulsion and first diluted emulsion may be sampled using capillaries. In other methods within the invention, dilution of the concentrated emulsion to form the first diluted emulsion may occur in a first dilution chamber, which may comprise a hollow, substantially vertical vessel, wherein the flow of concentrated emulsion and added continuous phase fluid optionally traverse the first dilution chamber from bottom to top of the chamber, although other flow patterns may be used, including counter-flow, cross-flow, and the like. Certain methods of the invention may control flow of fluid at the outlet of the droplet size measurement device employed, ensuring that the flow velocity through the measurement apparatus is at a suitable velocity for the measurement process used and that all of the flows are controlled through the tubing dilution chamber or chambers, and the like. Method may include calibrating all of the flow rate controlling valves.

Using sampling and dilution methods of the invention it is possible to achieve dilution ratios ranging from about 10:1 to about 10,000:1.

Another aspect of the invention are apparatus for carrying out the methods, one apparatus comprising:
(a) means for obtaining a sample of a concentrated emulsion comprising a dispersed phase and a continuous phase fluid;
(b) a droplet concentration measuring component fluidly connected to the means for obtaining a sample;
(c) a first dilution chamber fluidly connected to the droplet concentration measuring component; and
(d) optionally, a droplet size distribution measuring component fluidly connected to the first dilution chamber.

Apparatus within this aspect of the invention include those wherein the means for obtaining a sample is selected from hollow objects selected from tubing (for example capillary tubing), cup-shaped objects, catheter-like devices comprising a sample grabber, and pipettes (for example a glass micropipette). In certain apparatus embodiments, the droplet concentration measuring device and the droplet size distribution measuring components may be the same or different devices. Apparatus within the invention may comprise second or further dilution chambers. The means for obtaining the sample, the droplet concentration measuring component, the dilution chamber(s), and droplet size distribution measuring component may all be fluidly connected using tubing comprising materials selected from ferrous and non-ferrous metals, plastics, combinations thereof, and the like. Examples of suitable metal tubing include stainless steel tubing, copper tubing, and the like, while examples of suitable plastic tubing include polyethylene, polytetrafluoroethylene, and the like. The droplet size distribution measuring component may be selected from known devices, as further discussed herein. Apparatus within the invention may comprise strategically located flow rate controlling valves designed to produce substantially constant flow rates irrespective of pressure drop through sampling lines, and the diluting flow rate may be independent of any of the pressures in the supply or sampling lines.

Other apparatus of the invention include those including a seal between the sample tubing and/or dilution chamber(s) and means for sampling the emulsion or diluted versions thereof. In certain embodiments the seal may comprise a joint, for example a ball joint, having a substantially central passage therethrough, wherein the means for obtaining a sample of a concentrated emulsion or diluted emulsion may be positioned in the central passage. The joint may be an integral component of a pressurized sample probe defining a sample probe chamber. The joint may allow the distal end of the sample probe to be moved in 3-dimensional space, including in translational movements (x, y, z) or by cylindrical movements (circular, radial and translational) or equivalent, inside of the pipe or dilution chamber.

Sampling and dilution may be performed manually or automatically, for example, through computer control. The dilution chamber(s) may be fluidly connected to a system allowing inflow of a continuous phase fluid to effect dilution of the concentrated sample. Furthermore, despite the specific example provided in the detailed description herein, the relative physical positions of the means for sampling, dilution chamber(s), flow rate controlling valves, and droplet size distribution measuring component are not critical; inventive apparatus may be constructed in any manner that allows a concentrated emulsion sample to be obtained and move the concentrated emulsion into one or more dilution chambers so that it may be diluted to a droplet concentration of less than about 1000 ppm. Apparatus of the invention may be used to sample and dilute O/W and W/O emulsions, particularly from petroleum fluid pipelines under high pressure and high temperature conditions, although apparatus within this aspect of the invention are not so limited.

Apparatus and methods of the invention will become more apparent upon review of the detailed description of the invention and the claims that follow.

BRIEF DESCRIPTION OF THE DRAWINGS

The manner in which the objectives of the invention and other desirable characteristics may be obtained is explained in the following description and attached drawing in which.

Figure 1:
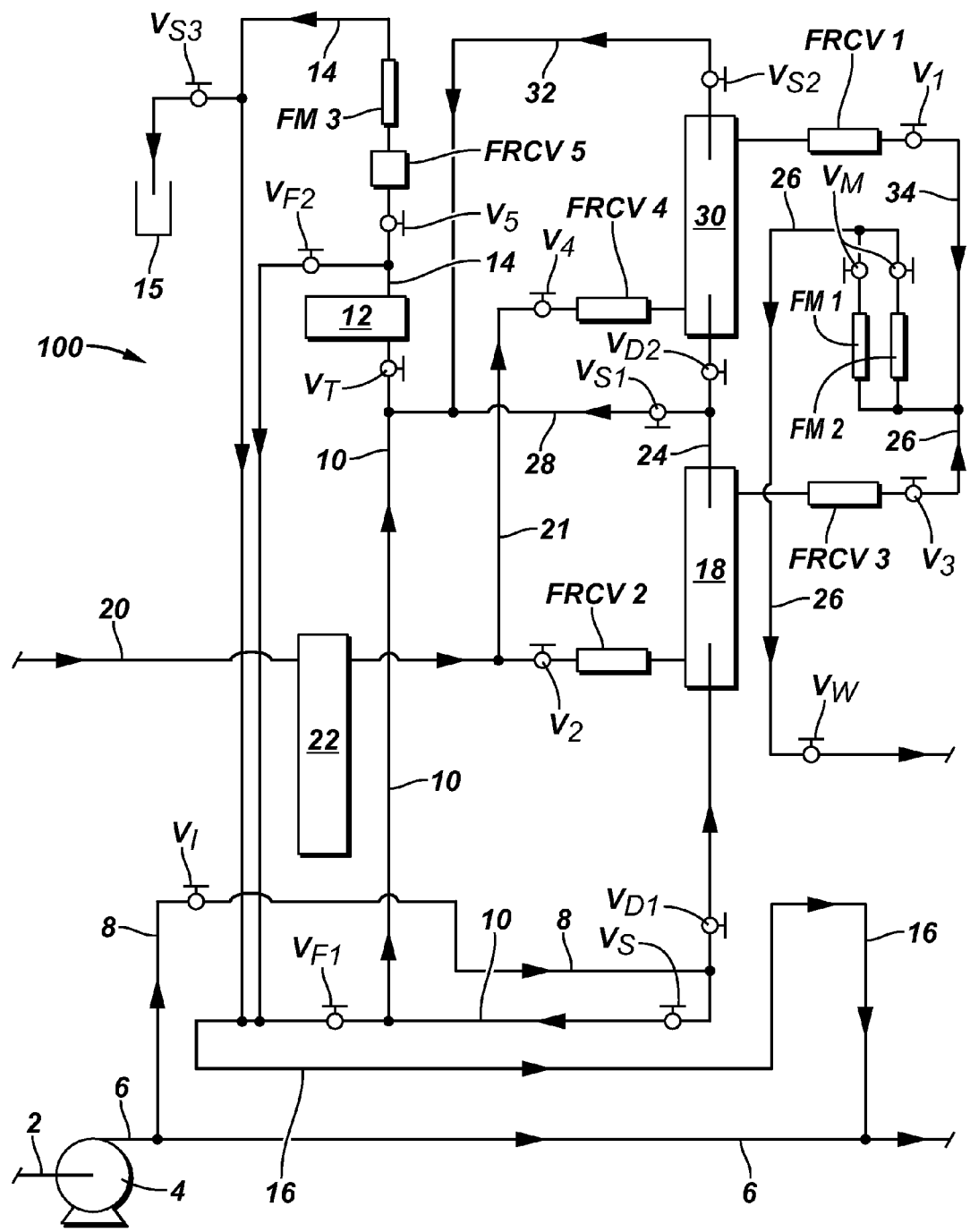
FIG. 1 is a schematic diagram of a system.

It is to be noted, however, that FIG. 1 is not to scale and illustrates only one typical embodiment of this invention, and is therefore not to be considered limiting of its scope, for the invention may admit to other equally effective embodiments.

DETAILED DESCRIPTION

In the following description, numerous details are set forth to provide an understanding of the present invention. However, it will be understood by those skilled in the art that the present invention may be practiced without these details and that numerous variations or modifications from the described embodiments may be possible.

Many oilfield phenomena and process performances are sensitive to the nature of the fluids present and flowing through the zone of interest. Often the flow is in the form of an emulsion of small oil droplets in water. This is most often seen after the fluid has passed through a choke, pump or other high-shear device, though can sometimes occur elsewhere, such as in the formation or main wellbore itself. The behavior of this fluid in subsequent processes, such as separators, coalescers or even simple plant elements such as pipes, pumps and valves can depend critically on the droplet sizes and the droplet size distribution. At present there exists no real-time in-line method for determining the droplet size distribution of an oil-in-water emulsion, or a water-in-oil emulsion, if the concentration of the minor component is greater than 1000 ppm. For concentrations less than 1000 ppm several devices exist that use different physical methods for determining the droplet size distribution. Direct imaging by light transmission is the method employed in a device manufactured by Jorin. A device manufactured by Malvern employs multi-angle two color light scattering. An apparatus manufactured by Beckman/Coulter uses an electrical sensing zone. Another known device employs ultrasonic scattering. In all of these known devices, the inability to analyze more concentrated emulsions is caused by the complex interpretation required when the particles are very close together, when secondary effects such as multiple scattering and/or shadowing start to occur. One possible way around this is to take a sample of the concentrated emulsion, optionally stabilize the concentrated emulsion with a suitable additive, such as one or more surfactants, and then dilute the resulting mixture with a pure sample of the continuous phase until one of the known methods can take a reading of the droplet size distribution.

Apparatus of the invention allow real-time, in-line sampling and controlled dilution of a flowing emulsion, so that a continuous measurement of the particle size distribution may be made. In the example discussed in reference to FIG. 1, the particle size analysis is made using a droplet size distribution apparatus known under the trade designation "ViPA", available from Jorin, however, any known particle or droplet size analysis apparatus able to provide droplet size distribution of droplets in emulsions wherein the droplets are present in concentration of 1000 ppm or less may be employed. Apparatus and methods of the present invention pertain to sample preparation prior to determining the droplet size distribution.

In general, and with reference to embodiment 100 illustrated in FIG. 1, a pipeline 2 carries a fluid to a device, such as a pump 4, which shears the fluid and produces an emulsion downstream in pipeline 6. Pump 4 and pipelines 2 and 6 are not features of the invention. In accordance with methods and apparatus of the invention, a sample of concentrated emulsion is taken via a capillary tube 8 and inlet valve $V_I$. It will be recognized by those skilled in the art that not all or the features in embodiment 100 may be necessary in all embodiments. First, a check is made that the emulsion really is too concentrated to make a droplet size analysis. A direct valve $V_S$ is opened, allowing the concentrated emulsion to traverse trough conduit 10, and a test valve $V_T$ is opened to allow the sample to flow into a droplet concentration measuring device, 12, and the concentrated emulsion is analyzed for droplet concentration. Sample exits droplet concentration measurement device 12 through a conduit 14, valve $V_5$, a flow rate controlling valve FRCV 5, and ultimately into conduit 16 to be returned to pipeline 6. A portion may be sampled through valve $V_{S3}$ into a container 15. If the emulsion is too concentrated, $V_S$ is closed and $V_{D1}$ is opened in line 8 leading the concentrated emulsion to a first dilution chamber 18, where the sample of concentrated emulsion is combined with substantially pure continuous phase, for example purified water, entering through a conduit 20, optional purifier 22, shutoff valve V2, and flow rate controlling valve FRCV 2. The FRCV's are designed to produce a constant flow rate irrespective of the pressure drop across them. Thus the diluting flow rate is independent of any of the pressures in the supply or sampling lines. In this embodiment, diluted emulsion passes vertically up chamber 18 and is sub-sampled at the top using a capillary 24, the majority going to waste by flowing through FRCV 3, shutoff valve $V_3$, flow meters FM 1 and FM 2, one or both flow meter valves Vm, a waste valve Vw, and conduit 26 to waste.

The sampled/diluted flow in capillary 24 may then be analyzed for droplet size distribution using device 12, such as the device known under the trade designation "ViPA" from Jorin, after passing through $V_{S1}$ conduit 28, and valve $V_T$ in conduit 10. If the diluted emulsion is still too concentrated for analysis, then $V_{S1}$ is closed and the flow of first diluted emulsion diverted though capillary 24 and opening valve $V_{D2}$ into second dilution chamber 30 for further dilution into chamber 2, where the process of dilution with further purified water, charged to 30 via conduit 21, open valve $V_4$, and flow rate controlling valve FRCV 4. Another flow rate controlling valve, FRCV 1, controls flow of the second diluted emulsion, directing the second diluted emulsion either through valve $V_{S2}$ and conduit 32, conduit 28, valve $V_T$ and test device 12; or to waste through valve $V_1$, conduit 34, conduit 26, flow meters FM 1 and FM 2, flow meter valves $V_m$, conduit 26, and valve $V_w$. Another flow rate controlling valve FRCV 5 on the outlet of the test device 12 and in conduit 14 ensures that the flow velocity through the measurement device 12 is at a suitable velocity for the measurement process and that flows are controlled through every component of the apparatus. By calibrating all of the FRCVs and using either one, two, or further stage dilution, it is possible to achieve dilution ratios ranging from about 10:1 to about 10,000:1.

Figure 2:
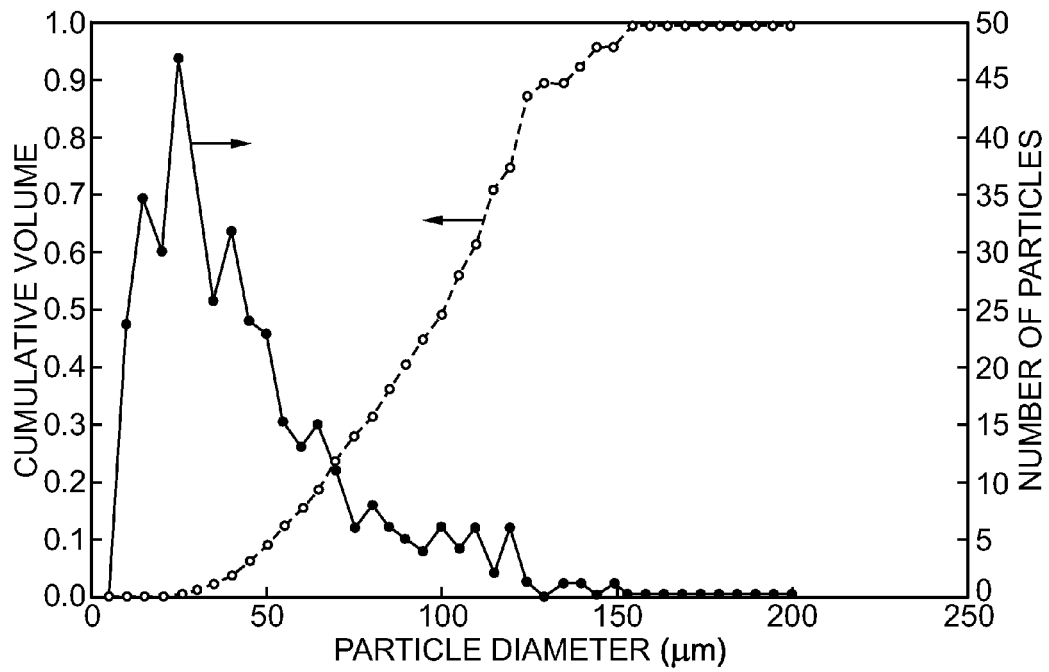
FIG. 2 is a plot of cumulative volume and number of particles versus particle diameter.
Figure 3:
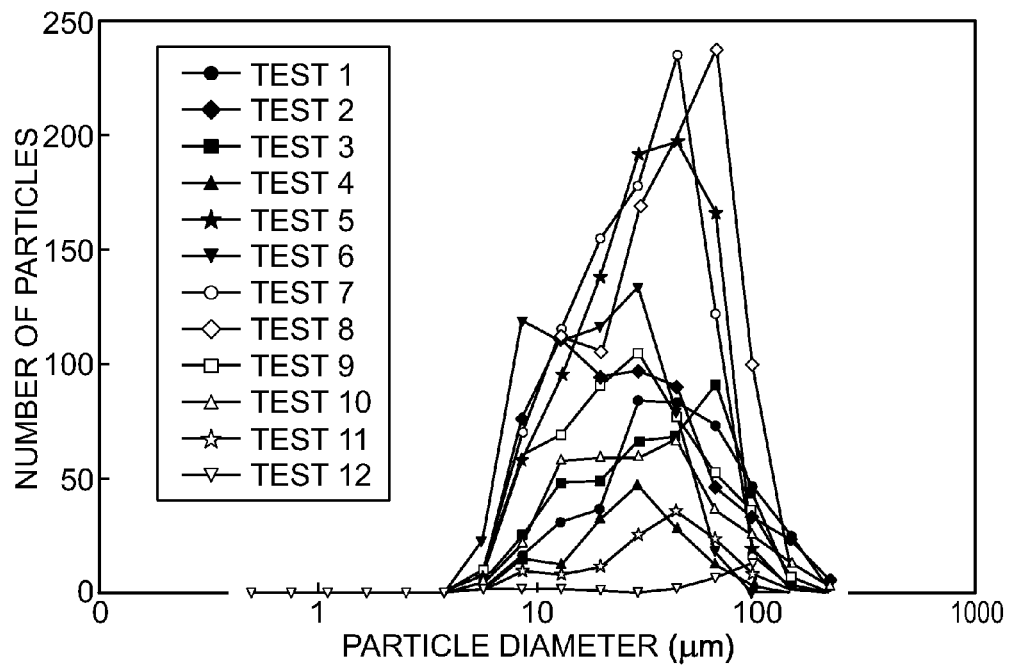
FIG. 3 is a plot of number of particles versus particle diameter.

FIG. 2 illustrates droplet size distribution in an oil-in-water emulsion and cumulative sample volume gathered downstream of an electrical submersible pump (ESP), the stream flowing at 3000 bpd [477 m$^3$/day] with a 20 percent oil (API 25) fraction. FIG. 3 illustrates similar data for a pump geometry comprising two mixed flow impellor pumps (known under the trade designation "Reda" from Schlumberger) which were 11 stage GN4000 pumps, and the oil was API 35. The tests were carried out at about 10 bar [1 MPa] and 20-40° C., however the apparatus and methods of the invention are not limited to these parameters, as there is no fluid mechanics reason why the apparatus and methods cannot work at any other pressure and temperature, assuming the conduits, valves, dilution chambers and other hardware components can withstand the temperatures and pressures. An important feature is that apparatus and methods of the invention may be used to sample and dilute unstable as well as stable concentrated emulsions. The fluid handling components are designed with fluid mechanics in mind so that the droplets in the concentrated emulsions are spread out before they get a chance to coalesce, and to keep the turbulence correct so that the droplets don't break up. Thus there is no need for any surfactants to be added, and the whole process may be performed continuously, rather than in batches. Furthermore, all of the detailed discussion of FIG. 1, and the test data reflected in FIGS. 2 and 3 have been for oil-in-water emulsions—hence in these embodiments the general direction of fluid flows is upwards and the diluting fluid is substantially pure water. If we were to reverse the density contrast—i.e., sample and dilute a water-in-oil emulsion, certain embodiments would benefit by building the apparatus "upside down", having the fluid flows going generally downwards and the diluting flow would be substantially pure oil. Similar considerations apply for other fluid systems (i.e., other than O/W and W/O emulsions).

If it is desired to stabilize or quasi-stabilize the concentrated emulsion prior to testing, one or more surfactants may be used. In these embodiments, the sample may be sent to waste, rather than back into the pipeline from which the concentrated emulsion sample was retrieved. Surfactants useful in the methods and apparatus of the invention include cationic, amphoteric, and zwitterionic surfactants and surfactant fluid systems such as betaine viscoelastic surfactant fluid systems. Certain shear recovery agents and other additives may also be present in the emulsions as sampled, or added to the samples. Particularly suitable zwitterionic surfactants may have the formula:

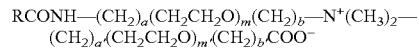

in which R is an alkyl group that contains from about 17 to about 23 carbon atoms which may be branched or straight chained and which may be saturated or unsaturated; a, b, a', and b' are each from 0 to 10 and m and m' are each from 0 to 13; a and b are each 1 or 2 if m is not 0 and (a+b) is from 2 to 10 if m is 0; a' and b' are each 1 or 2 when m' is not 0 and (a'+b') is from 1 to 5 if m is 0; (m+m') is from 0 to 14; and $CH_2CH_2O$ may also be $OCH_2CH_2$. Zwitterionic surfactants include betaines. The surfactants may be used at a concentration of about 0.5 to about 10%, preferably from about 1 to about 5%, and most preferably from about 1.5 to about 4.5%. Exemplary cationic viscoelastic surfactants include the amine salts and quaternary amine salts disclosed in U.S. Pat. Nos. 5,979,557, and 6,435,277 which have a common assignee as the present application and which are hereby incorporated by reference. Examples of suitable cationic viscoelastic surfactants include cationic surfactants having the structure:

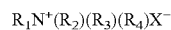

in which $R_1$ has from about 14 to about 26 carbon atoms and may be branched or straight chained, aromatic, saturated or unsaturated, and may contain a carbonyl, an amide, a retroamide, an imide, a urea, or an amine; $R_2$, $R_3$, and $R_4$ are each independently hydrogen or a $C_1$ to about $C_6$ aliphatic group which may be the same or different, branched or straight chained, saturated or unsaturated and one or more than one of which may be substituted with a group that renders the $R_2$, $R_3$, and $R_4$ group more hydrophilic; the $R_2$, $R_3$ and $R_4$ groups may be incorporated into a heterocyclic 5- or 6-member ring structure which includes the nitrogen atom; the $R_2$, $R_3$ and $R_4$ groups may be the same or different; $R_1$, $R_2$, $R_3$ and/or $R_4$ may contain one or more ethylene oxide and/or propylene oxide units; and $X^-$ is an anion. Mixtures of such compounds are also suitable. As a further example, $R_1$ is from about 18 to about 22 carbon atoms and may contain a carbonyl, an amide, or an amine, and $R_2$, $R_3$, and $R_4$ are the same as one another and contain from 1 to about 3 carbon atoms.

Cationic surfactants having the structure $R_1N^+(R_2)(R_3)(R_4)X^-$ may optionally contain amines having the structure $R_1N(R_2)(R_3)$. It is well known that commercially available cationic quaternary amine surfactants often contain the corresponding amines (in which $R_1$, $R_2$, and $R_3$ in the cationic surfactant and in the amine have the same structure). Concentrated emulsions may also optionally have added thereto one or more members of the group consisting of alcohols, glycols, organic salts, chelating agents, solvents, mutual solvents, organic acids, organic acid salts, inorganic salts, oligomers, polymers, co-polymers, and mixtures of these members.

Amphoteric viscoclastic surfactants are also suitable. Exemplary amphoteric viscoelastic surfactant systems include those described in U.S. Pat. No. 6,703,352, for example amine oxides. Mixtures of zwitterionic surfactants and amphoteric surfactants are suitable. An example is a mixture of about 13% isopropanol, about 5% 1-butanol, about 15% ethylene glycol monobutyl ether, about 4% sodium chloride, about 30% water, about 30% cocoamidopropyl betaine, and about 2% cocoamidopropylamine oxide.

Methods and apparatus of the invention for sampling and diluting a concentrated emulsion allow in-line, real-time analysis of the flow, while causing minimal disturbance of the flow, for example droplet size analysis in concentrated emulsions. The use of multiple flow rate controlling valves allows achievement of substantially constant and known dilution ratios. As mentioned previously, an important feature is that all of the flow rate controlling valves (or other flow rate controlling means as described herein) are downstream of the dilution, sampling and measurement process. Thus the fluid being tested does not feel any shear from any flow controlling device prior or during measurement of droplet size distribution. Rather than flow rate controlling valves, restriction orifices and/or simple manually-operated valves may be employed, but the flow rate through each of these is sensitive to the pressure of the purified continuous fluid supply and the sampled flow and would require more careful adjustment and calibration to control the dilution rate(s).

In embodiments of the invention, tubing, conduits, and vessels (for example the dilution chambers) may be formed from metal, plastic, glass or other ceramic material, or may be formed from composite of materials, such as a glass tube encased in metal or two metal tubes in a pipe-in-pipe configuration. The flow rate controlling valves, if used, may be automated, for example by use of a computer, and the valves may be hydraulically operated or step gear motors may be used to control the movement of flow control valves.

In certain embodiments, the entire apparatus may be temperature controlled. Sources of temperature control include liquid baths, liquid jackets, pettier devices, convection gas baths, and the like. For example, a convection air bath may be employed to control the temperature in the entire apparatus to within $\pm 1°$ C., and in certain embodiments within $\pm 0.1°$ C. If vibration is to be minimized, apparatus of the invention may be isolated from its surrounding to minimize vibration of the apparatus.

The concentrated emulsions may be liquid, supercritical, and may comprise gaseous components. The concentrated emulsion may be taken at elevated temperatures and pressures, including, but not limited to compositions comprising hydrocarbons (including sour hydrocarbons which may include hydrogen sulfide, mercaptans, and other sulfur-containing compounds), water, organic and/or inorganic solids, and may include micelles, macromolecules, globules, resins, asphaltenes, hydrocarbon and aqueous based fluids, drilling muds, frac fluids, and the like having multiple phases (solids and liquid). The sample composition may comprise one or more of each phase. The term "reservoir" may include hydrocarbon deposits accessible by one or more wellbores. A "wellbore" includes cased, cased and cemented, or open-hole wellbores, and may be any type of well, including, but not limited to, a producing well, a non-producing well, an experimental well, an exploratory well, and the like. Wellbores may be vertical, horizontal, any angle between vertical and horizontal, diverted or non-diverted, and combinations thereof, for example a vertical well with a non-vertical component. The phrase "high temperature, high pressure" means any temperature and pressure conditions that are above atmospheric pressure and above 20° C.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A method of sampling and diluting a concentrated flowing emulsion to form a dilute emulsion, the method comprising:
   providing a flow rate controlling valve which ensures a constant flow rate irrespective of pressure drop across the flow rate controlling valve;
   obtaining a sample of the concentrated flowing emulsion comprising a dispersed phase and a continuous phase fluid;
   measuring a droplet concentration of the dispersed phase in the sample, wherein the droplet concentration is greater than about 1000 ppm;
   continuously flowing a portion of the concentrated flowing emulsion for dilution in a dilution chamber and for droplet size measurement by a droplet size distribution measuring component;
   continuously diluting the continuously flowing portion of the concentrated flowing emulsion with a pure continuous phase fluid, forming a first diluted emulsion in the dilution chamber;
   and continuously flowing a portion of the first diluted emulsion to the droplet size distribution measuring component at the constant flow rate via the flow rate controlling valve being located downstream the droplet size distribution measuring component to ensure that a flow velocity through the droplet size distribution measuring component is at a suitable velocity for measuring the droplet size distribution.

2. The method of claim 1 further comprising measuring the droplet concentration of the first diluted emulsion, and if the droplet concentration of the first diluted emulsion is greater than 1000 ppm, performing one or more further dilutions with the pure continuous phase fluid, and re-measuring the droplet size distribution after each further dilution.

3. The method of claim 1 wherein the obtaining a sample comprises sampling the concentrated flowing emulsion using capillary tubing.

4. The method of claim 1 wherein the diluting of the portion of the concentrated flowing emulsion to form the first diluted emulsion comprises diluting the portion of the concentrated flowing emulsion in a first dilution chamber.

5. The method of claim 4 wherein the first dilution chamber comprises a hollow, vertical vessel, and wherein the diluting of the portion of the concentrated flowing emulsion to form the first diluted emulsion comprises flowing the portion of the concentrated flowing emulsion and the added continuous phase fluid from a bottom to a top of the vertical vessel.

6. The method of claim 1 further comprising diluting the portion of the concentrated flowing emulsion with an amount of the pure continuous phase fluid in order to achieve a dilution ratio in a range from about 10:1 to about 10,000:1.

7. The method of claim 1 wherein the concentrated flowing emulsion is selected from oil-in-water emulsions and water-in-oil emulsions.

8. The method of claim 6 further comprising combing the portion of the concentrated flowing emulsion with an additive to stabilize the portion of the concentrated flowing emulsion prior to diluting.

9. A method of measuring droplet sizes in a concentrated flowing emulsion comprising:
providing a flow rate controlling valve which ensures a constant flow rate irrespective of pressure drop across the flow rate controlling valve;
commencing continuous flow of a portion of the concentrated flowing emulsion via a conduit for additive addition, dilution and droplet size measurement by operating the flow rate controlling valve located downstream a droplet size distribution measuring component, the concentrated flowing emulsion being selected from oil in-water emulsions and water-in-oil emulsions;
continuously combining the portion of the concentrated flowing emulsion with an additive to form a stabilized concentrated flowing emulsion;
continuously diluting the stabilized concentrated flowing emulsion with a pure continuous phase fluid, forming a first diluted emulsion; and
continuously flowing the first diluted emulsion to the droplet size distribution measuring component and, by operating the flow rate controlling valve, ensuring that a flow velocity through the droplet size distribution measuring component is at a suitable velocity for measuring the droplet size distribution.

10. The method of claim 1 further comprising providing a second flow rate controlling valve for supplying the pure continuous phase fluid to the dilution chamber, the second flow rate controlling valve being calibrated to ensure a second constant flow rate irrespective of pressure drop across the second flow rate controlling valve.

11. The method of claim 10 further comprising providing a third flow rate controlling valve for supplying the pure continuous phase fluid to another dilution chamber, the third flow rate controlling valve being calibrated to ensure a third constant flow rate irrespective of pressure drop across the third flow rate controlling valve wherein the second constant flow rate and the third constant flow rate provide a dilution factor for determining at least in part a range of dilution ratios.

12. The method of claim 1 further comprising directing a portion of the first diluted emulsion from the dilution chamber to a waste stream.

13. The method of claim 12 further comprising providing a second flow rate controlling valve for the waste stream, the second flow rate controlling valve being calibrated to ensure a second constant flow rate irrespective of pressure drop across the second flow rate controlling valve.

14. The method of claim 1 further comprising continuously flowing the portion of the first diluted emulsion to the droplet size distribution measuring component via a capillary tube in fluid communication with the dilution chamber.

* * * * *